US012305881B2

(12) United States Patent
Chen et al.

(10) Patent No.: US 12,305,881 B2
(45) Date of Patent: May 20, 2025

(54) AIR PURIFIER AND AIR VENTILATION DEVICE HAVING THE SAME

(71) Applicant: TRIPLE WIN TECHNOLOGY(SHENZHEN) CO.LTD., Shenzhen (CN)

(72) Inventors: Shin-Wen Chen, New Taipei (TW); Jing-Wei Li, Guangdong (CN); Sheng-Jie Ding, Guangdong (CN); Jian-Chao Song, Guangdong (CN)

(73) Assignee: TRIPLE WIN TECHNOLOGY(SHENZHEN) CO.LTD., Shenzhen (CN)

(*) Notice: Subject to any disclaimer, the term of this patent is extended or adjusted under 35 U.S.C. 154(b) by 489 days.

(21) Appl. No.: 17/672,958

(22) Filed: Feb. 16, 2022

(65) Prior Publication Data

US 2022/0290891 A1    Sep. 15, 2022

(30) Foreign Application Priority Data

Mar. 9, 2021  (CN) .......................... 202120500201.3

(51) Int. Cl.
| | |
|---|---|
| *B01D 53/22* | (2006.01) |
| *A61L 9/20* | (2006.01) |
| *B01D 46/00* | (2022.01) |
| *F24F 8/108* | (2021.01) |
| *F24F 8/20* | (2021.01) |
| *F24F 8/22* | (2021.01) |
| *F24F 13/28* | (2006.01) |

(52) U.S. Cl.
CPC ................ *F24F 13/28* (2013.01); *A61L 9/20* (2013.01); *B01D 46/0028* (2013.01); *B01D 46/0036* (2013.01); *F24F 8/108* (2021.01); *F24F 8/20* (2021.01); *F24F 8/22* (2021.01); *A61L 2209/14* (2013.01); *A61L 2209/15* (2013.01); *B01D 2265/023* (2013.01); *B01D 2279/65* (2013.01)

(58) Field of Classification Search
CPC .... F24F 8/20; F24F 8/108; F24F 13/28; F24F 8/22; B01D 2279/65; B01D 2265/023; B01D 46/0028; B01D 46/0036; A61L 2209/14; A61L 2209/15; A61L 9/20
See application file for complete search history.

(56) References Cited

U.S. PATENT DOCUMENTS

| | | | | |
|---|---|---|---|---|
| 11,471,634 | B1 * | 10/2022 | Lee ................... | A61M 16/0616 |
| 11,602,576 | B1 * | 3/2023 | Kaplan ............... | F04B 39/16 |
| 2006/0131511 | A1 * | 6/2006 | Ehlers ................ | C02F 1/325 |
| | | | | 250/373 |

(Continued)

FOREIGN PATENT DOCUMENTS

CN        201650804 U   * 11/2010

OTHER PUBLICATIONS

Machine translation of CN 201650804 U Nov. 24, 2010 Li N (Year: 2010).*

*Primary Examiner* — Anthony R Shumate
(74) *Attorney, Agent, or Firm* — ScienBiziP, P.C.

(57) ABSTRACT

An air purifier includes a ventilation cover, a filtering component, and a sterilization component. The ventilation cover has an air inlet and an air outlet. The filtering component is fixed at the air outlet. The sterilization component is disposed between the air inlet and the air outlet. An air ventilation device may include the air purifier.

16 Claims, 8 Drawing Sheets

(56) References Cited

U.S. PATENT DOCUMENTS

| | | | | |
|---|---|---|---|---|
| 2008/0115473 | A1* | 5/2008 | Miller | B01D 46/10 |
| | | | | 55/385.6 |
| 2015/0053703 | A1* | 2/2015 | Kreidler | A61B 50/30 |
| | | | | 220/745 |
| 2019/0063770 | A1* | 2/2019 | Vairamudi | F24F 11/89 |
| 2020/0047106 | A1* | 2/2020 | Taylor | B01D 46/0005 |
| 2021/0162342 | A1* | 6/2021 | He | B01D 53/78 |
| 2021/0379410 | A1* | 12/2021 | Anthony | A62B 7/10 |
| 2022/0090801 | A1* | 3/2022 | Zeng | A61L 9/20 |
| 2022/0170651 | A1* | 6/2022 | Martensen | F24F 8/22 |
| 2022/0176291 | A1* | 6/2022 | Yang | A61L 9/014 |
| 2022/0241451 | A1* | 8/2022 | Johnston | F24F 8/22 |
| 2023/0083721 | A1* | 3/2023 | Wang | A61L 9/122 |
| | | | | 422/121 |
| 2023/0285889 | A1* | 9/2023 | Cha | B01D 46/001 |
| 2023/0341139 | A1* | 10/2023 | Woods | F24F 8/80 |

\* cited by examiner

AIR PURIFIER AND AIR VENTILATION DEVICE HAVING THE SAME

FIELD

The subject matter herein generally relates to air purification, and more particularly, to an air purifier and an air ventilation device having the air purifier.

BACKGROUND

Ventilation systems are used for air exchange between indoor and outdoor environments. However, all ventilation ports of the ventilation system are interconnected to each other, so viruses or bacteria carried by air may be transmitted through the whole ventilation system. Moreover, air purifiers in the ventilation systems may not effectively block or kill viruses. Thus, potential risks of Coronavirus spreading are increased.

BRIEF DESCRIPTION OF THE DRAWINGS

Implementations of the present technology will now be described, by way of embodiment, with reference to the attached figures.

DETAILED DESCRIPTION

Figure 1:
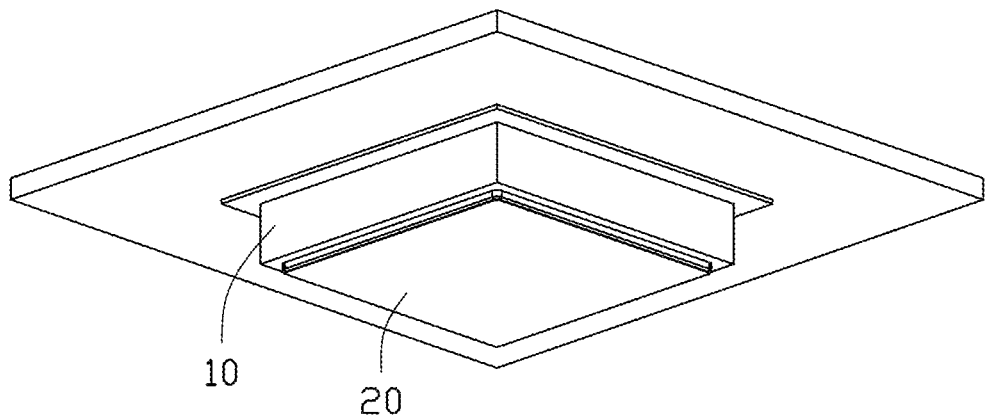
FIG. 1 is a diagrammatic view of an embodiment of an air purifier according to the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and members have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series, and the like.

Embodiment 1

Figure 2:
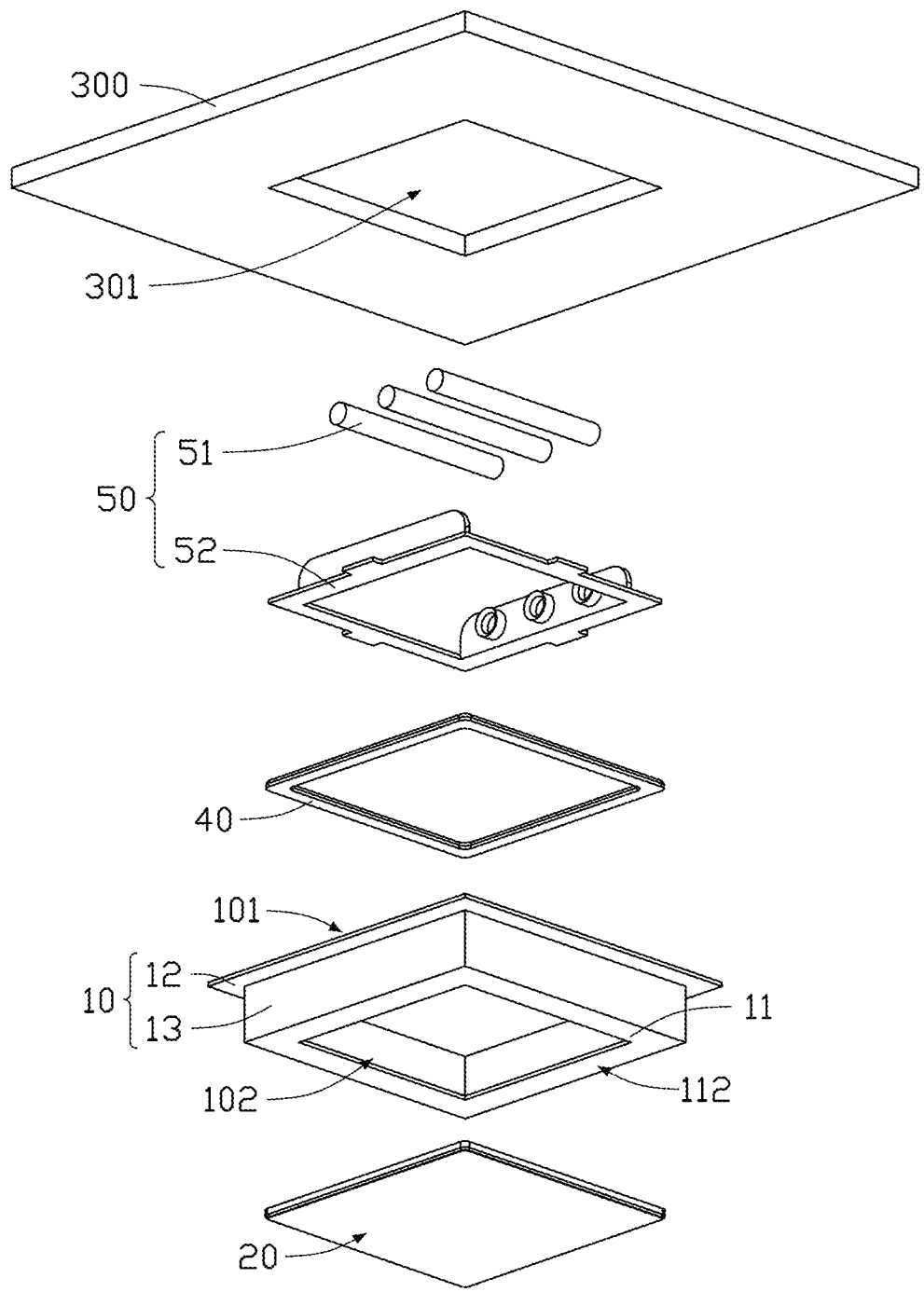
FIG. 2 is␣an exploded view of the air purifier of FIG. 1.

Referring to FIGS. 1 and 2, an embodiment of an air purifier 100 is provided, which includes a ventilation cover 10, a filtering component 20, and a sterilization component 50. The ventilation cover 10 has an air inlet 101 and an air outlet 102. The sterilization component 50 is disposed between the air inlet 101 and the air outlet 102. The filtering component 20 is fixed at the air outlet 102. In at least one embodiment, the air purifier 100 can be fixed to a vent 301 of a ceiling 300, and the air inlet 101 is connected to the vent 301 of the ceiling 300.

Figure 4:
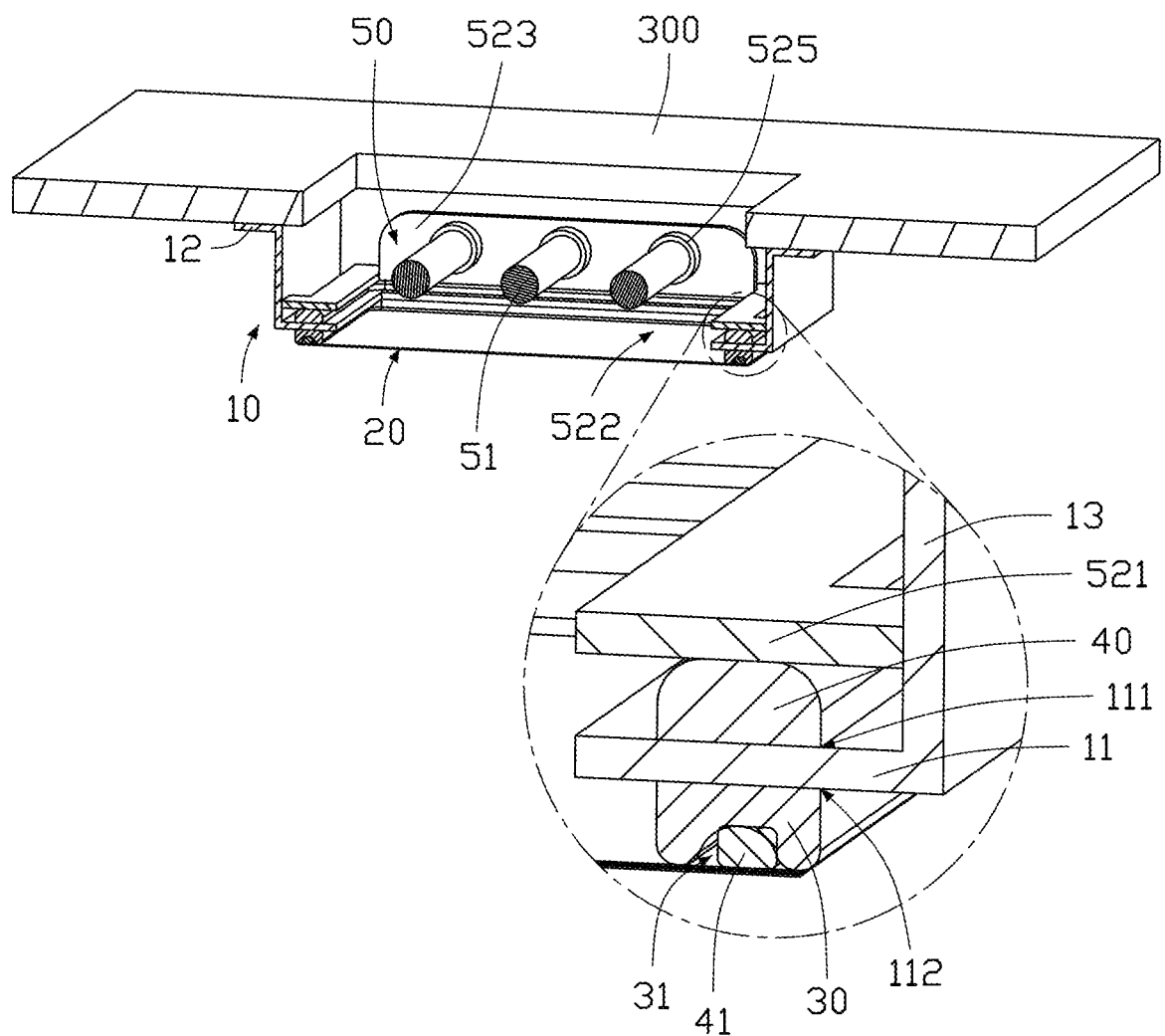
FIG. 4 is a cross-sectional view of the air purifier of FIG. 1.

Referring to FIGS. 2 and 4, the ventilation cover 10 includes a base plate 12 and a plurality of sidewalls 13 formed on the base plate 12. The base plate 12 defines the air inlet 101, and the sidewalls 13 cooperatively define the air outlet 102. The end of each sidewall 13 away from the base plate 12 extends inward to form an inner flange 11. The inner flange 11 includes a first surface 111 facing the air inlet 101 and a second surface 112 opposite to the first surface 111. In at least one embodiment, the sterilization component 50 is disposed on the first surface 111. The filtering component 20 is disposed on the second surface 112. In other embodiments, the sterilization component 50 and the filtering component 20 may both be disposed on the second surface 112. The sterilization component 50 may also be fixed at any position between the air inlet 101 and the air outlet 102 of the ventilation cover 10, ensuring that air entering the ventilation cover 10 can flow from the sterilization component 50 to the filtering component 20.

In at least one embodiment, the sterilization component 50 includes a mounting frame 52 and a plurality of ultraviolet lamps 51. The mounting frame 52 includes a support plate 521, a first mounting plate 523, and a second mounting plate 524 (shown in FIG. 3). The first mounting plate 523 and the second mounting plate 524 can fix the support plate 521 in the ventilation cover 10. The support plate 521 defines a first ventilation hole 522 passing through the support plate 521, and the first ventilation hole 522 is connected to the air inlet 101 and the air outlet 102. The support plate 521 is fixed on the first surface 111. The first mounting plate 523 and the second mounting plate 524 are opposite to each other, and fixed on a surface of the support plate 521 facing the air inlet 101.

Figure 3:
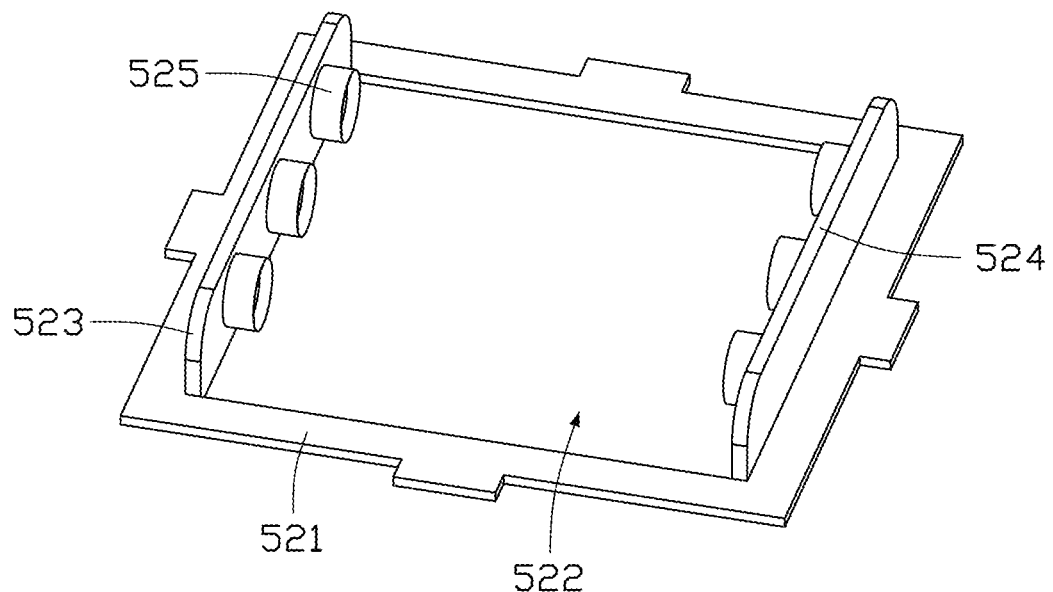
FIG. 3 is a diagrammatic view of a mounting frame of the air purifier of FIG. 1.

Referring to FIGS. 3 and 4, in at least one embodiment, each ultraviolet lamp 51 is a lamp tube, and the ultraviolet lamps 51 are arranged in parallel and disposed above the first ventilation hole 522. An air channel is defined between two adjacent ultraviolet lamps 51. A plurality of mounting rings 525 are disposed on the first mounting plate 523 and the second mounting plate 524. The ultraviolet lamps 51 are fixed on the mounting frame 52 through the mounting rings 525.

Figure 5:
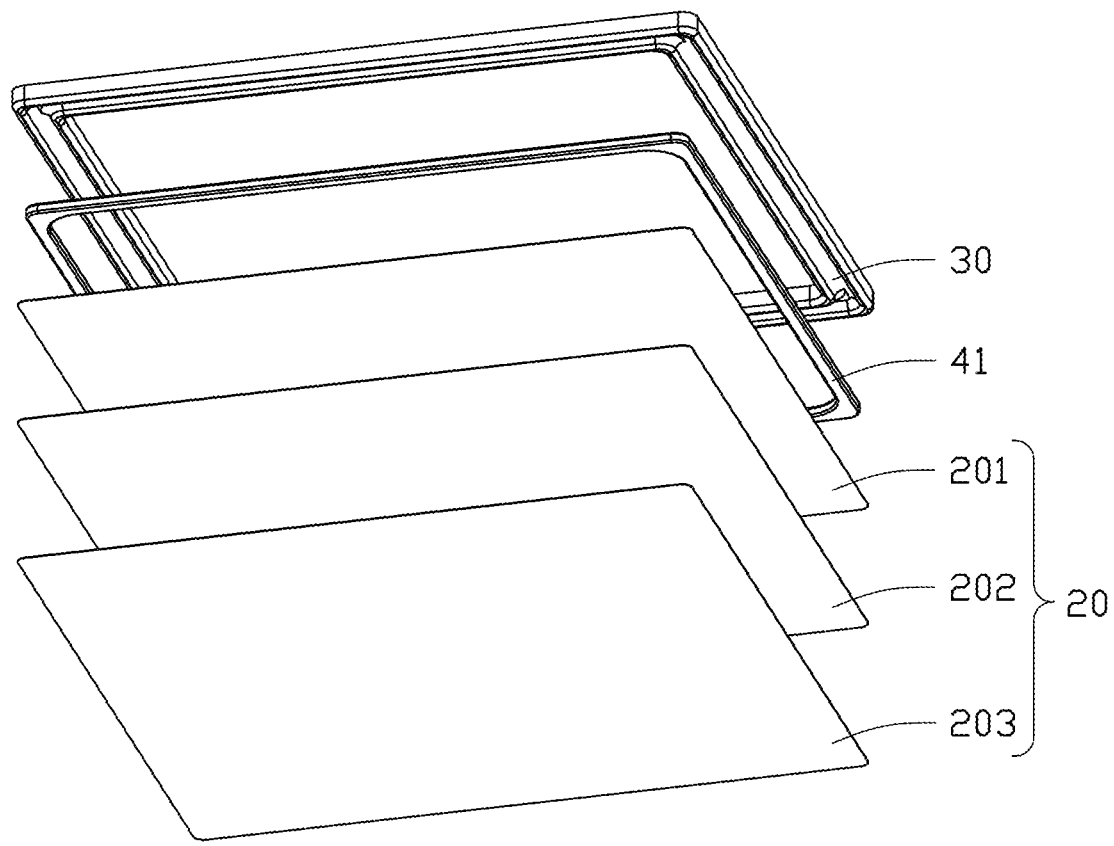
FIG. 5 is an exploded view of a filtering component of the air purifier of FIG. 1.

Referring to FIGS. 4 and 5, the filtering component 20 includes a breathable layer 201, an anti-virus layer 202, and an activated carbon layer 203 stacked in that order. The breathable layer 201 is disposed on the second surface 112 of the inner flange 11. The breathable layer 201 can be made of high breathable non-woven fabric. The anti-virus layer 202 can be made of melt blown cloth, which can block viruses in air. An elastic member 30 is also arranged between the filtering component 20 and the second surface 112 of the inner flange 11, so that a gap between the filtering component 20 and the ventilation cover 10 is sealed, which prevents unfiltered air from flowing indoors from the gap. The elastic member 30 can be made of soft rubber, and the elastic member 30 and the filtering component 20 can be integrally formed by thermoplastic.

In order to better fix the filtering component 20, the air purifier 100 also includes a first magnetic member 40 and a second magnetic member 41, and each of the first magnetic member 40 and the second magnetic member 41 can be annular. The first magnetic member 40 is disposed between the first surface 111 of the inner flange 11 and the sterilization component 50, that is, the first magnetic member 40 is between the support plate 521 and the first surface 111 of the inner flange 11. The elastic member 30 is connected to the second surface 112 of the inner flange 11. A surface of the elastic member 30 away from the inner flange 11 defines a receiving groove 31. The second magnetic member 41 is received in the receiving groove 31, and the second magnetic member 41 is disposed between the elastic member 30 and the filtering component 20. The magnetic absorbing force between the first magnetic member 40 and the second magnetic member 41 can fix the filtering component 20 to the ventilation cover 10. When it is needed to replace the filtering component 20 for a new one, the filtering component 20 is removed, and the new filtering component 20 can be directly fixed on the inner flange 11 through the magnetic absorbing force of the first magnetic member 40 and the second magnetic member 41.

In the present disclosure, when air enters the ventilation cover 10, the sterilization component 50 in the ventilation cover 10 kills bacteria or viruses in the air. The sterilized air is further processed by the filtering component 20 to filter out dust or other impurities in the air. As such, fresh air can be delivered indoors.

Embodiment 2

Embodiment 2 differs from embodiment 1 in the structure of the sterilization component 50.

Figure 6:
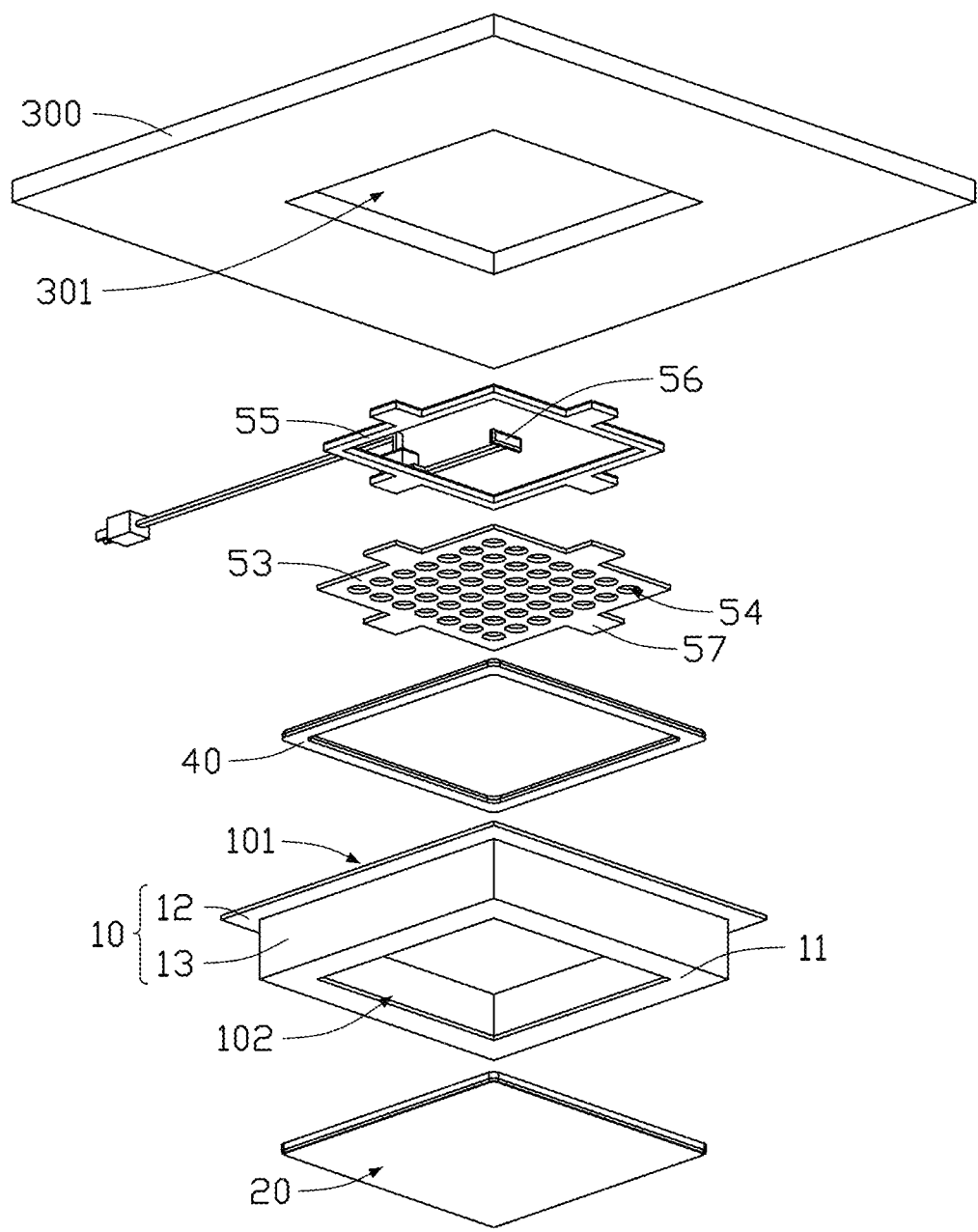
FIG. 6 is an exploded view of another embodiment of an air purifier according to the present disclosure.
Figure 7:
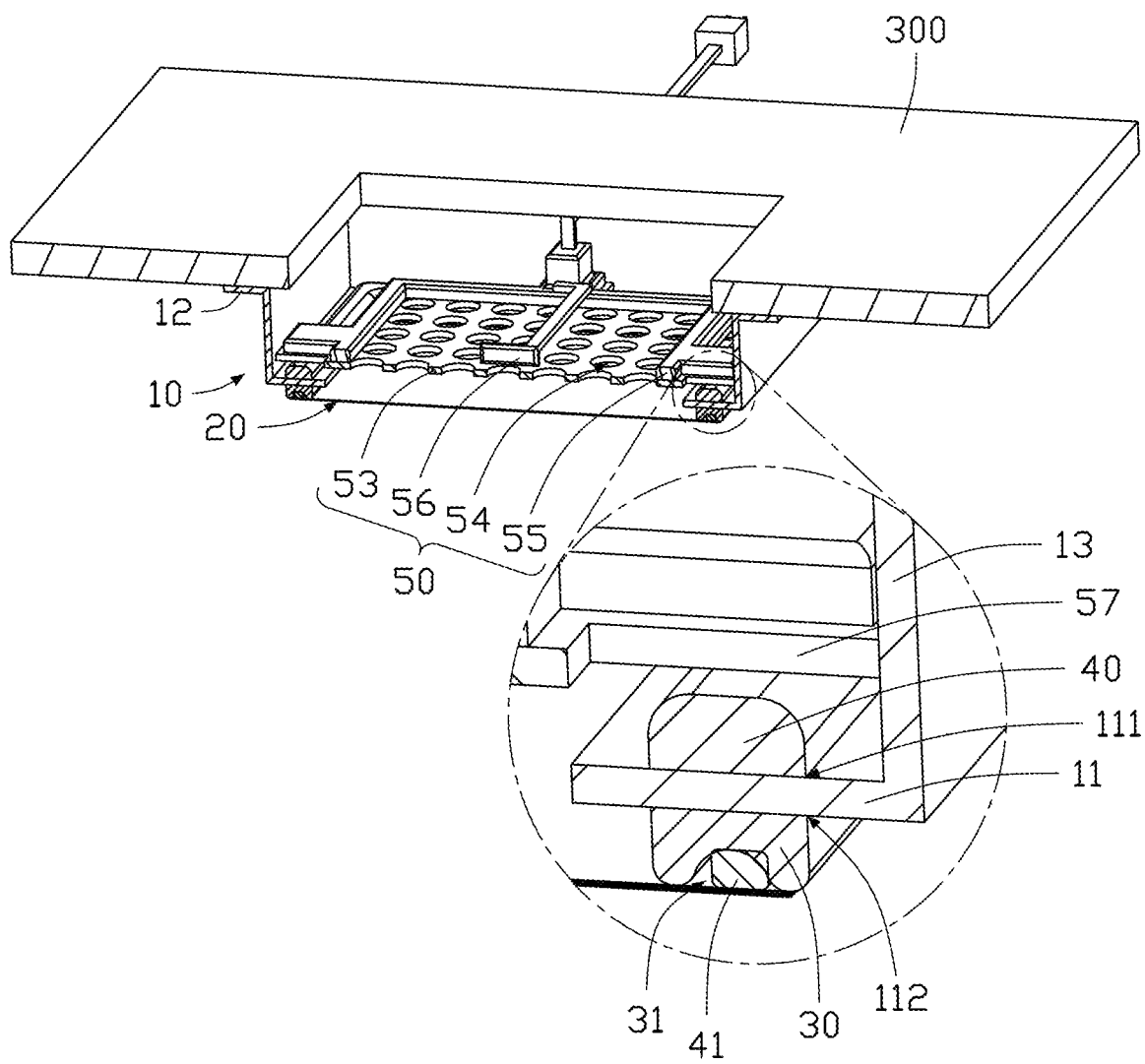
FIG. 7 is a cross-sectional view of the air purifier of FIG. 6.

Referring to FIGS. 6 and 7, the sterilization component 50 includes a heat guiding plate 53, an electric heating plate 55, and a temperature sensor 56. The heat guiding plate 53 defines a plurality of second ventilation holes 54 passing through the heat guiding plate 53. The second ventilation holes 54 are connected to the air inlet 101 and the air outlet 102. The heat guiding plate 53 is fixed on the first surface 111 of the inner flange 11. The edges of the heat guiding plate 53 facing towards the sidewalls 13 of the ventilation cover 10 include a plurality of blocks 57. The blocks 57 are disposed on the first magnetic member 40, so that the heat guiding plate 53 is fixed in the ventilation cover 10.

Referring to FIGS. 6 and 7, the electric heating plate 55 is disposed on a surface of the heat guiding plate 53 away from the inner flange 11. The electric heating plate 55 is disposed between two adjacent second ventilation holes 54 or at the edge of the heat guiding plate 53. The electric heating plate 55 is connected to a power supply, and can provide heat source for the heat guiding plate 53. Through the heat transfer between the electric heating plate 55 and the heat guiding plate 53, the heat guiding plate 53 reaches a certain temperature, thereby killing the viruses in the air. In order to monitor the temperature of the heat guiding plate 53, the temperature sensor 56 is disposed on the heat guiding plate 53.

Figure 8:
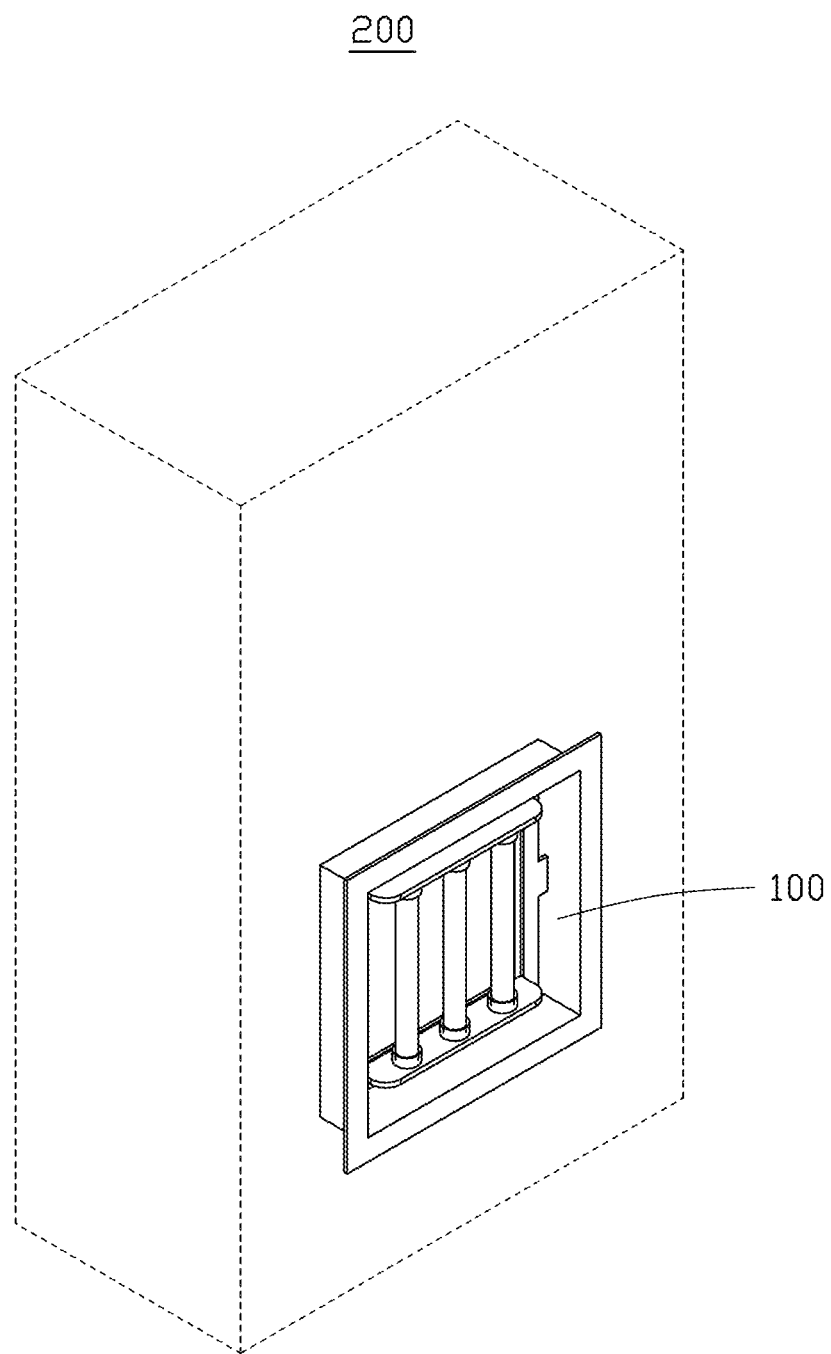
FIG. 8 is a diagrammatic view of an embodiment of an air ventilation device according to the present disclosure.

Referring to FIG. 8, the present disclosure further provides an air ventilation device 200, which includes the air purifier 100. The air ventilation device 200 can be an air renewal device or an indoor air conditioner.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present embodiments to the full extent indicated by the plain meaning of the terms in which the appended claims are expressed.

What is claimed is:

1. An air purifier, comprising:
   a ventilation cover having an air inlet and an air outlet;
   a filtering component fixed at the air outlet;
   a sterilization component disposed between the air inlet and the air outlet; and
   a first magnetic member and a second magnetic member, wherein the ventilation cover comprises a base plate and a plurality of sidewalls formed on the base plate, ends of the plurality of sidewalls away from the base plate extend inward to form an inner flange; the inner flange comprises a first surface facing the air inlet and a second surface opposite to the first surface; the filtering component is disposed on the second surface, and the sterilization component is fixed on the first surface; wherein an elastic member is disposed between the filtering component and the second surface;
   wherein the first magnetic member is disposed between the first surface and the sterilization component; the elastic member defines a receiving groove, the second magnetic member is disposed in the receiving groove; the filtering component is fixed on the ventilation cover through a magnetic absorbing force between the second magnetic member and the first magnetic member.

2. The air purifier of claim 1, wherein the sterilization component comprises a mounting frame and an ultraviolet lamp; the mounting frame comprises a support plate, a first mounting plate, and a second mounting plate; the support plate defines a first ventilation hole communicated with the air inlet and the air outlet; the first mounting plate and the second mounting plate are arranged on a same surface of the support plate, and opposite to each other; the ultraviolet lamp is fixed between the first mounting plate and the second mounting plate.

3. The air purifier of claim 1, wherein the sterilization component comprises a heat guiding plate, an electric heating plate, and a temperature sensor; the heat guiding plate defines a plurality of second ventilation holes communicated with the air inlet and the air outlet; the heat guiding plate is fixed on the first surface; the electric heating plate is disposed on a surface of the heat guiding plate away from the inner flange; the electric heating plate is disposed between adjacent two of the plurality of second ventilation holes; the temperature sensor is disposed on the heat guiding plate, and configured to sense a temperature of the heat guiding plate.

4. The air purifier of claim 1, wherein the sterilization component comprises a heat guiding plate, an electric heating plate, and a temperature sensor; the heat guiding plate defines a plurality of second ventilation holes communicated with the air inlet and the air outlet; the heat guiding plate is fixed on the first surface; the electric heating plate is disposed on a surface of the heat guiding plate away from the inner flange; the electric heating plate is disposed at edges of the heat guiding plate facing towards the plurality of sidewalls; the temperature sensor is disposed on the heat guiding plate, and configured to sense a temperature of the heat guiding plate.

5. The air purifier of claim 4, wherein the edges of the heat guiding plate comprise a plurality of blocks disposed on the first surface.

6. The air purifier of claim 1, wherein the filtering component comprises a breathable layer, an anti-virus layer, and an activated carbon layer stacked in that order; the breathable layer is disposed on the second surface.

7. The air purifier of claim 6, wherein the elastic member is integrally formed with the filtering component.

8. The air purifier of claim 1, wherein each of the first magnetic member and the second magnetic member is annular.

9. An air ventilation device, comprising:
an air purifier, comprising:
a ventilation cover having an air inlet and an air outlet;
a filtering component fixed at the air outlet; and
a sterilization component disposed between the air inlet and the air outlet; and
a first magnetic member and a second magnetic member,
wherein the ventilation cover comprises a base plate and a plurality of sidewalls formed on the base plate, ends of the plurality of sidewalls away from the base plate extend inward to form an inner flange; the inner flange comprises a first surface facing the air inlet and a second surface opposite to the first surface; the filtering component is disposed on the second surface, and the sterilization component is fixed on the first surface; wherein an elastic member is disposed between the filtering component and the second surface;
wherein the first magnetic member is disposed between the first surface and the sterilization component; the elastic member defines a receiving groove, the second magnetic member is disposed in the receiving groove; the filtering component is fixed on the ventilation cover through a magnetic absorbing force between the second magnetic member and the first magnetic member.

10. The air ventilation device of claim 9, wherein the sterilization component comprises a mounting frame and an ultraviolet lamp; the mounting frame comprises a support plate, a first mounting plate, and a second mounting plate; the support plate defines a first ventilation hole communicated with the air inlet and the air outlet; the first mounting plate and the second mounting plate are arranged on a same surface of the support plate, and opposite to each other; the ultraviolet lamp is fixed between the first mounting plate and the second mounting plate.

11. The air ventilation device of claim 9, wherein the sterilization component comprises a heat guiding plate, an electric heating plate, and a temperature sensor; the heat guiding plate defines a plurality of second ventilation holes communicated with the air inlet and the air outlet; the heat guiding plate is fixed on the first surface; the electric heating plate is disposed on a surface of the heat guiding plate away from the inner flange; the electric heating plate is disposed between adjacent two of the plurality of second ventilation holes; the temperature sensor is disposed on the heat guiding plate, and configured to sense a temperature of the heat guiding plate.

12. The air ventilation device of claim 9, wherein the sterilization component comprises a heat guiding plate, an electric heating plate, and a temperature sensor; the heat guiding plate defines a plurality of second ventilation holes communicated with the air inlet and the air outlet; the heat guiding plate is fixed on the first surface; the electric heating plate is disposed on a surface of the heat guiding plate away from the inner flange; the electric heating plate is disposed at edges of the heat guiding plate facing towards the plurality of sidewalls; the temperature sensor is disposed on the heat guiding plate, and configured to sense a temperature of the heat guiding plate.

13. The air ventilation device of claim 12, wherein the edges of the heat guiding plate comprise a plurality of blocks disposed on the first surface.

14. The air ventilation device of claim 9, wherein the filtering component comprises a breathable layer, an antivirus layer, and an activated carbon layer stacked in that order; the breathable layer is disposed on the second surface.

15. The air ventilation device of claim 14, wherein the elastic member is integrally formed with the filtering component.

16. The air ventilation device of claim 9, wherein each of the first magnetic member and the second magnetic member is annular.

* * * * *